United States Patent [19]

Daggy et al.

[11] Patent Number: 5,422,101
[45] Date of Patent: Jun. 6, 1995

[54] CHOLESTEROL LOWERING DRINK MIX COMPOSITIONS

[75] Inventors: Bruce P. Daggy; Lee A. Hord, both of Mason, Ohio

[73] Assignee: The Procter & Gamble Company, Cincinnati, Ohio

[21] Appl. No.: 61,926

[22] Filed: May 14, 1993

[51] Int. Cl.⁶ ............................................. A61K 31/785
[52] U.S. Cl. ................................. 424/78.01; 424/78.1
[58] Field of Search ............................................ 424/78.1

[56] References Cited

U.S. PATENT DOCUMENTS

| | | | |
|---|---|---|---|
| Re. 32,811 | 12/1988 | Rudin | 424/195.1 |
| 906,709 | 12/1908 | Heintz | 424/195.1 |
| 2,060,336 | 11/1936 | Near et al. | 99/131 |
| 3,148,114 | 9/1964 | Fahrenbach et al. | 167/55 |
| 3,455,714 | 7/1969 | Bishop et al. | 106/205 |
| 4,172,120 | 10/1979 | Todd et al. | 424/78.1 |
| 4,321,263 | 3/1982 | Powell et al. | 424/195 |
| 4,341,805 | 7/1982 | Chaudhary | 426/481 |
| 4,459,280 | 7/1984 | Colliopoulos et al. | 424/35 |
| 4,511,561 | 4/1985 | Madaus et al. | 424/195.1 |
| 4,548,806 | 10/1985 | Colliopoulos et al. | 424/35 |
| 4,551,331 | 11/1985 | Rudin | 424/195.1 |
| 4,557,938 | 12/1985 | Sander et al. | 426/453 |
| 4,565,702 | 1/1986 | Morley et al. | 426/93 |
| 4,619,831 | 10/1986 | Sharma | 426/93 |
| 4,639,367 | 1/1987 | Mackles | 424/45 |
| 4,731,246 | 3/1988 | Chavkin et al. | 424/195.1 |
| 4,737,364 | 4/1988 | Kalogris | 424/195.1 |
| 4,747,881 | 5/1988 | Shaw et al. | 106/209 |
| 4,784,861 | 11/1988 | Gori | 426/74 |
| 4,812,315 | 3/1989 | Tarabishi | 424/466 |
| 4,824,672 | 4/1989 | Day et al. | 424/195.1 |
| 4,828,842 | 5/1989 | Furst et al. | 424/480 |

FOREIGN PATENT DOCUMENTS

| | | | |
|---|---|---|---|
| 105195 | 4/1984 | European Pat. Off. | A61L 2/06 |
| 144644 | 6/1985 | European Pat. Off. | A23L 1/308 |
| 285201 | 10/1988 | European Pat. Off. | A61K 35/78 |
| 323666 | 7/1989 | European Pat. Off. | A61K 31/785 |
| 362926 | 4/1990 | European Pat. Off. | A61K 35/78 |
| 412604 | 2/1991 | European Pat. Off. | A23L 1/00 |
| 2616329 | 12/1988 | France | A61K 35/78 |
| WO80/00658 | 4/1980 | WIPO | A61K 9/00 |
| WO85/01441 | 4/1985 | WIPO | A61K 35/78 |
| WO93/13801 | 7/1993 | WIPO | A61K 45/06 |

OTHER PUBLICATIONS

Physicians Desk Reference for Nonprescription Drugs, 10th Edition, pp. 641–642 (1989): "Orange Flavor Metamucil®"; Strawberry Flavor Metamucil®; Sugar Free Orange Flavor Metamucil®; Sugar Free Lemon–Lime Flavor Effervescent Metamucil®; Sugar Free Orange Flavor Effervescent Metamucil®; sold by The Procter & Gamble Company.
Fybogel® Orange, sold by Reckitt & Colman.
Sunrise Smooth Metamucil® (Citrus and Orange Flavored; Regular and Sugar Free), sold by The Procter & Gamble Company.

Primary Examiner—Thurman K. Page
Assistant Examiner—Peter F. Kulkosky
Attorney, Agent, or Firm—Mary Catherine Poland; Kathleen M. Harleston; Douglas C. Mohl

[57] ABSTRACT

Psyllium husk-containing drink mix compositions comprising psyllium husk, an anion exchange resin, and edible, water soluble salts. The edible, water soluble salts are present at a level sufficient to reduce the gellation rate of the psyllium husk and anion exchange resin-containing composition when dispersed in an aqueous solution.

18 Claims, No Drawings

CHOLESTEROL LOWERING DRINK MIX COMPOSITIONS

BACKGROUND OF THE INVENTION

The present invention relates to drink mix compositions useful for reducing serum cholesterol levels comprising psyllium husk, an anion exchange resin, and edible, water soluble salts. The salt provides the benefit of reducing the gellation rate of the drink mix compositions when dispersed in an aqueous solution. Preferred salts are neutral in flavor such that the drink mix composition is perceived by the consumer as being "unflavored".

High blood cholesterol levels are associated with life threatening cardiovascular diseases. Cholestyramine and colestipol are drugs used in treating hypercholesterolemia. These drugs are known as basic anion exchange resins. They help to lower blood cholesterol levels apparently by binding to bile acids in the intestine. It is believed that this in turn causes an increase in hepatic metabolism of cholesterol to replenish the bile acids lost to complexation with the anion exchange resins.

Cholestyramine is usually dosed at four grams, one to six times daily. At the present time cholestyramine is commercially available as Questran ® and Questran ® Light (manufactured by the Bristol-Myers Company) in a four gram unit dose powder packet or in bulk powder, and as Cholybar ® (manufactured by Parke Davis) wherein one chewable bar contains four grams of cholestyramine. [*Physicians Desk Reference*, 46th Edition, pages 710–712 and 1705–1706 (1992).]

Colestipol is usually administered at five to thirty grams daily given once or in divided doses. Colestipol is commercially available under the tradename Colestid ® (colestipol hydrochloride granules, manufactured by The Upjohn Company). It is sold in a five gram unit dose powder packet or in bulk powder. [*Physicians Desk Reference*, 46th Edition, pages 2328–2329 (1992)].

Recent research has demonstrated that psyllium seed husk fiber is also effective in reducing human serum cholesterol levels. In addition, psyllium seed husk fiber has been found to be effective in controlling blood glucose levels in diabetics and in providing laxation and normalization of bowel function. Products containing psyllium seed husk are known (for example, Metamucil ®, sold by The Procter & Gamble Company).

Drink mix compositions containing psyllium husk and an anion exchange resin begin to gel once dispersed in an aqueous solution with an accompanying increase in the viscosity of the drink solution. The gellation rate is further increased relative to psyllium alone, believed to be due to ionic interaction of the anionic psyllium husk with the polycationic anion exchange resin in the aqueous solution. The consumer of such drink mix suspension must drink the liquid suspension in a relatively short period of time (less than about two minutes) in order to avoid having to drink an aesthetically unacceptable high viscosity liquid. After this time period the solution is likely to be considered too thick to enjoy drinking or too difficult to drink.

One possible way to control the rate of gellation is by using acids to reduce the pH of the drink mix solution. However, typical acids can impart too strong a flavor (e.g., a sour or bitter flavor) to the solution. This is especially a concern at higher acid levels which may be desired to maximize the reduction in gellation rate. In addition, the acids must be consistent with the flavor system being used in the composition. Obviously, a highly acidic medium is not suitable for flavor systems which require neutral or basic conditions. Also, except in certain controlled circumstances, acids are not suited for use in unflavored systems.

For these reasons, there continues to be a need for psyllium/anion exchange resin-containing drink mix compositions having reduced (slower) gellation rates. It has been discovered by the present invention that the gellation rate of such drink mix compositions in an aqueous solution can be slowed by adding a sufficient amount of an edible, water soluble salt. This discovery is useful, for example, for allowing the use of less acid or no acid (to reduce or eliminate the acid characteristic of drink compositions), to permit a wider variety of flavor systems (including "unflavored" versions of such drink mix compositions), and to further reduce the gellation rate for compositions containing higher levels of acid.

It is therefore an object of the present invention to provide improved drink mix compositions containing psyllium and an anion exchange resin (e.g., cholestyramine) having reduced gellation rates in aqueous solution and/or improved aesthetics. It is also an object to provide such drink mix compositions which are unflavored or are not highly acidic flavored systems.

These and other objects of the present invention will become readily apparent from the detailed description which follows.

All percentages and ratios used herein are by weight unless otherwise specified. Screen mesh sizes used herein are based on U.S. standards.

SUMMARY OF THE INVENTION

The present invention relates to serum cholesterol lowering drink mix compositions. Such compositions comprise: (a) from about 10% to about 90% psyllium husk; (b) from about 10% to about 90% of anion exchange resin; (c) from about 0.1% to about 50% edible, water soluble salt at a level whereby the gellation rate of the drink mix composition in an aqueous solution is reduced; and (d) from about 0% to about 90% other excipients; and wherein further said compositions are in a form mixable with a liquid to form a suspension of the psyllium husk and anion exchange resin.

DETAILED DESCRIPTION OF THE INVENTION

The drink mix compositions of the present invention are compositions useful for reducing serum cholesterol levels containing psyllium and an anion exchange resin in any form suitable for mixing with a liquid to form a psyllium husk/anion exchange resin suspension for oral consumption. Preferred form is a dry powder in bulk or unit dose form which readily mixes and disperses in a liquid. The components of the compositions according to the present invention, and representative amounts, are described in detail as follows.

Psyllium Husk:

The psyllium husk used in the present invention is from psyllium seeds, from plants of the Plantago genus. Various species such as *Plantago lanceolate, P. rugelii*, and *P. major* are known. Commercial psyllium husk include the French (black; *Plantago indica*), Spanish (*P. psyllium*) and Indian (blonde; *P. ovata*). Indian (blonde) psyllium husk is preferred for use herein. Also preferred is psyllium husk which is at least about 85% pure, more preferably at least about 90% pure, and most preferably at least about 95% pure.

The psyllium husk is obtained from the seed coat of the psyllium seeds. It is typical to remove the seed coat from the rest of the seed by, for example, slight mechanical pressure, and then to use only the seed coat. The seed coat is preferably removed and sanitized by methods known in the art. Preferred is sanitized psyllium seed husk having substantially intact cell structure, the sanitization having been accomplished by methods such as ethylene oxide sanitization and superheated steam sanitization (as taught in U.S. Pat. No. 4,911,889, issued Mar. 27, 1990 to Leland et. al., the disclosures of which are incorporated herein by reference in their entirety). It is also preferred that the psyllium husk herein have reduced particle size (as taught, for example, in U.S. Pat. No. 5,149,541, issued Sep. 22, 1992, to Leis, Jr. et al., the disclosures of which are incorporated herein by reference in their entirety).

Preferred for use in the present invention compositions is small particle size psyllium husk. The term "small particle size psyllium husk", as used herein, means that the psyllium husk utilized in compositions of the present invention have a substantial amount of small particle size psyllium husk such that the psyllium husk comprises psyllium husk particle sizes distributed such that more than about 90% is smaller than about 45 mesh. More preferably, more than about 80% is smaller than about 50 mesh, further preferred is more than about 80% is smaller than about 60 mesh and most preferably at least about 80% is smaller than about 80 mesh. Further preferred particle sizes are distributed as follows: less than about 25% larger than about 60 mesh, and at least about 40% smaller than about 80 mesh. More preferred are particle size distribution of: less than about 10% larger than about 60 mesh, at least about 40% within th about 80 mesh to about 200 mesh, and less than about 50% smaller than about 200 mesh. Particle sizes and particle size distributions may be readily determined by one of ordinary skill in the art, for example by sieving using an Alpine Laboratory Air Jet Sieve (sold by Alpine American Corp., Natick Mass. ).

The drink mix compositions preferably contain from about 10% to about 90%, more preferably from about 20% to about 90%, most preferably from about 25% to about 75%, of psyllium husk.

Anion Exchange Resin:

The term "anion exchange resin", as used herein, means any resinous material having cationic moieties such that the material is safe and therapeutically effective for treating hypercholesterolemia (at a reasonable benefit/risk ratio within the scope of sound medical judgement). Preferred anion exchange resins useful herein include cholestyramine, colestipol, and mixtures thereof.

Cholestyramine is a strongly basic anion exchange resin which contains quaternary ammonium functional groups attached to a styrenedivinylbenzene copolymer. [The Merck Index, 10th Edition, published by Merck & Co., No. 2182 (1983), incorporated by reference herein in its entirety]. Cholestyramine resin-containing compositions are available commercially in powder form under the trade names Cuemid ® (Merck, Sharp & Dome) and Questran ® and Questran ® Light (Bristol Laboratories division of Bristol-Myers). Cholestyramine is commercially available as Duolite AP-143 resin (Rohm & Haas Co.).

Colestipol is an insoluble, high molecular weight basic anion-exchange copolymer of diethylene triamine and 1-chloro-2,3-expoxypropane with approximately 1 out of 5 amine nitrogens protonated (chloride form). [The Merck Index, 11th edition, published by Merck & Co., No. 2472 (1989), incorporated by reference herein in its entirety]. Colestipol is commercially available as colestipol hydrochloride granules under the trade name Colestid ® (Upjohn).

The anion exchange resin in the present invention compositions typically comprises from about 10% to about 90% by weight of the pharmaceutical composition of the present invention, and preferably from about 20% to about 90%. Most preferred is the anion exchange resin comprising from about 25% to about 75% by weight of the pharmaceutical composition of the present invention.

Edible, Water Soluble Salts:

The term "edible, water soluble salts" as used herein, means any salt material, organic or inorganic, which is soluble in water (under normal use conditions for a psyllium/anion exchange resin-containing drink mix composition) and having a pKa of greater than about 5, and which is safe for ingestion by humans. Examples of edible, water soluble salts include magnesium sulfate, calcium chloride, calcium sulfate, calcium citrate malate, potassium chloride, sodium chloride, potassium sulfate, sodium sulfate, zinc chloride, zinc sulfate, potassium sotbate, and mixtures thereof. Preferred are the salts of divalent cations (e.g. calcium, magnesium, zinc) and especially those salts of strong inorganic acids (e.g., magnesium sulfate, calcium sulfate, calcium chloride, zinc sulfate, zinc chloride, and mixtures thereof).

As used herein, the term "calcium citrate malate" refers to a mixture or (preferably) a complex of calcium, citrate and malate. The calcium citrate malate may consist of a mixture of calcium citrate and calcium malate, a complex of calcium containing citrate and malate ligands, a mixture of a calcium salt with citric acid and malic acid, or combinations thereof. Calcium citrate malate is a highly bioavailable source of calcium. Calcium citrate malate for use herein may be preformed as a powder or can be formed in situ. Preferred calcium citrate malate have calcium:citrate:malate molar ratios of about 6:2:3 and 4:2:3. Methods for making calcium citrate malate are described in the following documents, incorporated by reference herein in their entirety: Japanese Patent Specification SHO 56-97248, Kawai, published Aug. 5, 1981; U.S. Pat. No. 4,722,847, issued to Heckert, Feb. 2, 1988; and U.S. Pat. No. 5,186,965, issued to Fox et al., Feb. 16, 1993.

It is necessary for the purposes of the present invention for the amount of the the edible, water soluble salt to be present in an amount sufficient to reduce the gellation rate of the drink mix composition relative to the compositions without the added salt. This is especially important for salts of certain organic acids which at certain levels can have the unwanted effect of increasing the gellation rate of psyllium alone suspensions (i.e., make the solution thicker, faster), but when used at other levels may provide the desired benefit of reducing the gellation rate according to the present invention.

Determination of whether the level of salt present in the psyllium husk/anion exchange resin-containing composition is at a level whereby the gellation rate of the psyllium/anion exchange resin-containing drink mix composition in an aqueous solution is reduced, as required by the present invention, is readily made by simple experimentation. For example, it is possible to compare the rate of viscosity increase for a composition containing the salt versus the composition containing the same components but not the edible, water soluble salt. If the rate of gellation is slowed by the addition of the amount of salt used, a sufficient level of the salt(s) as taught by the present invention is present. Methods and equipment for measuring gellation rates and viscosity of liquids are known, and such measurements and determinations can easily be made by one skilled in the art. For example, the Brookfield Viscometer may be used as is exemplified hereinafter.

Compositions of the present invention therefore may comprise from about 0.1% to about 50% edible, water soluble salts, preferably from about 0.1% to about 20%, and more preferably from about 0.5% to about 5% by weight of the drink mix composition.

Other Excipients:

Other excipients in the compositions of the present invention must be safe for oral administration to humans, and may be chosen by one of ordinary skill in the art as appropriate for the drink mix form and use intended for the product. Psyllium-containing drink mix products, methods for making, and other excipients useful for these products, are described more fully, for example, in U.S. Pat. No. 4,459,280, to Colliopoulos et al., issued Jul. 10, 1984; U.S. Pat. No. 4,548,806, to Colliopoulos et al., issued Oct. 22, 1985; U.S. Pat. No. 4,321,263, to Powell et al., issued Mar. 23, 1982; and U.S. Pat. No. 4,828,842, to Furst et al., issued May 9, 1989; all of which are incorporated by reference herein in their entirety. The drink mix compositions of the present invention comprise from about 0% to about 90%, preferably from about 1% to about 60%, and more preferably from about 2% to about 50%, of other excipients.

Most preferred are products of the present invention in dry powder form suitable for mixing in a liquid to form a psyllium/anion exchange resin-containing drink. Preferred other excipients for such powder forms are known and are also described in detail, for example, in U.S. Pat. Nos. 4,459,280 and 4,548,806, incorporated hereinbefore by reference. Preferred are such powders (preferably sugar free) comprising maltodextrin. Also especially preferred are powders comprising agglomerates of psyllium and/or coated psyllium, especially agglomerated with maltodextrin and/or sucrose.

Agglomerating materials preferred for use herein are known. These agglomerating materials include those selected from the group consisting of water dispersible hydrolyzed starch oligosaccharide, mono-saccharide, di-saccharide, polyglucose, polymaltose, and mixtures thereof. Compositions of the present invention preferably comprise from about 0.5% to about 20% of agglomerating material coating on said psyllium husk, preferably from about 1% to about 10%, and more preferably from about 1% to about 5%.

Hydrolysis of starch may be accomplished by a reaction of either acid, enzymes (e.g., alpha-amylase, beta-amylase or amyloglucosidase), or a combination of the two either together or reacted in series. The hydrolysis will follow different pathways depending on whether acids or enzymes are used. The result is a mixture of oligosaccharides which may be separated for their different properties. The resulting separated water dispersible (preferably soluble) hydrolyzed starch oligosaccharides are classified by their reducing sugar content, i.e., the mono- or di-saccharides such as glucose or fructose.

The percent reducing sugar content in the particular hydrolyzed starch oligosaccharide is measured on a weight/weight basis as the Dextrose Equivalent (or "D.E."). Hydrolyzed starch oligosaccharides with a D.E. of from 0 to 20 are called maltodextrins. The solid maltodextrins have low to moderate sweetness, low to moderate hygroscopicity, solubility in water and alcohol, and have reduced browning. Above a D.E. of about 20 the hydrolyzed starch oligosaccharides are called syrup solids. The syrup solids are soluble but have a more noticeable sweetness and are more hygroscopic. Above a D.E. of about 30, the syrup solids become less desirable for use herein. A preferred water dispersible hydrolyzed starch oligosaccharide therefore has a D.E. of from about 0 to about 30. A preferred maltodextrin has a D.E. of from about 5 to about 20, more preferably about 10 (i.e., a reducing sugar content ratio of 10% w/w of the oligosaccharide).

The mono-saccharides are those carbohydrates that in general are aidehyde-alcohols or ketone alcohols that are a hexose or pentose and have a sweet taste. They are readily soluble in water and form crystalline solids. Examples of the di-saccharides are those carbohydrates which yield two mono-saccharides on hydrolysis. Examples of di-saccharides are lactose, sucrose and maltose.

Preferred compositions of the present invention comprise an edible acid as part or all of the optional other excipients. The term "edible acids", as used herein, means any water soluble acid material having a $PK_a$ of less than about 5, preferably within the range of from about 2 to about 5, and is safe for ingestion by humans. Examples of edible acids include, but are not limited to, citric acid, ascorbic acid, malic acid, succinic acid, tartaric acid, phosphoric acid, monopotassium phosphate and mixtures thereof. Preferred are ascorbic acid, phosphoric acid, malic acid, and citric acid, with citric acid being most preferred.

The compositions of the present invention typically comprise from about 0.1% to about 25% edible acid, preferably from about 0.1% to about 10%, and more preferably from about 0.1% to about 5%. Also preferred are compositions containing less than about 2% edible acid, more preferably less than about 1% edible acid, and most preferably less than about 0.5% edible acid.

Preferred compositions of the present invention are those which have some or all of the edible acid coated on the psyllium husk, and further preferably such that the psyllium husk is agglomerated. Agglomerated psyllium husk is described in European Patent Application No. 412,604, published Feb. 13, 1991, and incorporated by reference herein in its entirety. Preferred single layer coating of the psyllium husk is achieved by utilizing equipment (referred to herein as single pass fluidizing powder wetting apparatus) which operates preferably by dropping a dry blend psyllium-containing material through a highly turbulent annular zone formed by a cylindrical wall and a rotating shaft with variously pitched attached blades. An edible acid-containing solution is preferably sprayed into this zone to contact a dry psyllium-containing blend. The resulting coated, preferably agglomerated, psyllium husk is dropped to a fluid bed dryer where the added solvent is removed. An example of this equipment is the Bepex Turboflex Model No. TFX-4 (sold by Bepex Corporation; Minneapolis, Minn.) with a six square foot bed vibrating fluid bed dryer (sold by Witte Corporation, Inc.; Washington, N.J.).

The psyllium-containing blend preferably comprises from about 25% to about 100% of psyllium. Optional components for the psyllium-containing blend include, but are not limited to, edible acid, sweetening agents (preferably low calorie sweetening agents, including, but not limited to, aspartame, saccharin, cyclamate, acesulfame, and mixtures thereof), coloring agents, agglomerating materials (especially maltodextrin), dietary fibers such as brans (e.g., wheat bran; oat bran; rice bran)and/or pharmaceutical agents (e.g., nonsteroidal anti-inflammatories; aspirin; sennosides). Some or all of the edible, water soluble salt and/or anion exchange resin may also be included in the psyllium-containing blend. As noted hereinbefore, it is preferred that the psyllium-containing blend be dry, but it is possible to utilize suitable solvents (e.g., alcohols and/or water) if one is careful, especially if water is utilized, not to cause substantial hydration and swelling of the psyllium, since this is expected to adversely affect the rate at which psyllium husk can interact with water or other fluids.

The solution mixture preferably comprises one or more edible acids to be sprayed onto the psyllium-containing blend along with also preferably comprising some or all of the edible, water soluble salt. This may be prepared by selecting a liquid (e.g., alcohol and/or water) as appropriate for the materials being coated onto the psyllium husk. However, it is preferred that water be utilized. Preferred is also spraying the solution mixture onto a dry psyllium-containing blend. Preferably, when a spraying technique is used, the solution mixture is an aqueous solution comprising from about 1% to about 50% (preferably from about 10% to about 25%) of the edible, water soluble salt and also from about 0% to about 50% (preferably from about 1% to about 20%) of edible acid. It is also optionally possible to repeat the coating and drying steps, thereby building up a coating on the psyllium husk which comprises several thin layers of the materials. In addition, other optional materials may be present in the solution mixture, such as coloring agents, pharmaceutical agents, and mixtures thereof.

Other methods for preparing compositions according to the present invention include dry blending the ingredients and other means of multiple layer coating of the psyllium husk. The latter may be accomplished by using, for example, fluid bed agglomerating equipment such as the Fluid Air, Inc. Model 0300 Granulator-Dryer.

Method of Treatment:

The method of treatment herein comprises orally administering to a human or lower animal patient in need of having a lowered blood cholesterol level a safe and effective amount of an aqueous liquid suspension of a psyllium/anion exchange resin-containing composition according to the present invention. The term "safe and effective amount", as used herein, means an amount of a psyllium fiber/anion exchange resin composition high enough to significantly positively modify the hypercholesterolemic condition being treated, but low enough enough to avoid serious side effects (at a reasonable benefit/risk ratio), within the scope of sound medical judgement. The safe and effective amount will vary with the age and physical condition of the patient being treated, the nature of the condition, the duration of treatment, the nature of concurrent therapy, and like factors within the knowledge and expertise of the attending physician. However, a patient in need of such treatment will typically receive from 4 g to about 24 g of the anion exchange resin daily and from 1 g to 30 g of psyllium husk.

The following examples further describe and demonstrate embodiments within the scope of the present invention. These examples are given solely for the purpose of illustration and are not to be construed as limitations of the present inventions as many variations thereof are possible without departing from the spirit and scope.

EXAMPLE 1

| EXAMPLE 1 | |
|---|---|
| Components | % in formula |
| Psyllium Mucilloid[a] | 40.60 |
| Cholestyramine Resin[b] | 45.10 |
| Citric Acid | 7.30 |
| Orange Flavor | 3.40 |
| Sodium Citrate | 1.70 |
| Aspartame | 0.62 |
| Calcium Chloride | 1.10 |
| Coloring | 0.09 |

[a] Psyllium husk of particle size approximately 100% through 80 mesh.
[b] Supplied by Rohm & Haas.

The composition is prepared by dry blending the ingredients. Consumption of 8.86 g of this composition twice daily by a person in need of cholesterol reduction, as a suspension in 8 ounces of water, provides 4 g of cholestyramine and 3.6 g of psyllium effective for reducing serum cholesterol.

EXAMPLE 2

To evaluate the value of adding various levels of edible, water soluble salts, the following comparative testing was conducted to evaluate the rate of viscosity increase for small particle size psyllium husk and cholestyramine suspended in a citric acid solution. The suspensions were prepared using the following components:

| | Weight %[d] | | | | |
|---|---|---|---|---|---|
| Suspension #: | 1 | 2 | 3 | 4 | 5 |
| psyllium[a] | 45.6 | 44.8 | 44.3 | 44.8 | 44.3 |
| cholestyramine[b] | 53.3 | 52.5 | 51.9 | 52.5 | 51.09 |
| citric acid[c] | 1.11 | 1.09 | 1.08 | 1.09 | 1.08 |
| $CaCl_2 \cdot 2H_2O$ | — | — | — | 1.64 | 2.70 |
| $MgSO_4 \cdot 7H_2O$ | — | 1.64 | 2.70 | — | — |

[a] Approximately 100% smaller than about 80 mesh; 8.2 g added in each suspension.
[b] 9.6 g added in each suspension.
[c] Citric acid: 20 g of 1% aqueous citric acid (by weight), was first diluted with water to give a total weight of 480 g.
[d] Weight % in the table is prior to water addition.

A dry blend of all the components (except for citric acid which was predissolved in the water) was added to the 480 g citric acid solution with 30 seconds of stirring in a 600 ml beaker. The weight of cholestyramine and psyllium added was kept constant in each suspension. [The weight % of cholestyramine and psyllium changed across the various suspensions due to the presence or absence of $CaCl_2$ or $MgSO_4$.] The viscosity of the suspension was measured using a Brookfield Viscometer (Model #RVT; Spindle 1; 10 RPM). The viscosity of the suspensions at various times were as follows:

| Suspension #: | 1 | 2 | 3 | 4 | 5 |
|---|---|---|---|---|---|
| Time (seconds) | Viscosity (centipoise) | | | | |
| 60 | 412 | 385 | 338 | 360 | 300 |
| 90 | 497 | 425 | 420 | 420 | 370 |
| 120 | 587 | 500 | 502 | 505 | 450 |
| 150 | 667 | 590 | 582 | 590 | 505 |

What is claimed is:

1. A psyllium husk/anion exchange resin-containing drink mix composition comprising:
   (a) from about 10% to about 90% psyllium husk;
   (b) from about 10% to about 90% of an anion exchange resin which is safe and therapeutically effective for treating hypercholesterolemia;
   (c) from about 0.1% to about 50% edible, water soluble salt selected from the group consisting of magnesium sulfate, calcium chloride, calcium sulfate, calcium citrate malate, potassium chloride, sodium chloride, potassium sulfate, sodium sulfate, zinc chloride, zinc sulfate, potassium sorbate, and mixtures thereof at a level whereby the gellation rate of the psyllium husk/anion exchange resin-containing drink mix composition in an aqueous solution is reduced; and
   (d) from about 0% to about 90% other excipients; and wherein further said composition is in a form mixable with a liquid to form a suspension of the psyllium husk and the artion exchange resin.

2. The composition according to claim 1 wherein the other excipients comprise from about 0.1% to about 25% edible acid by weight of the composition.

3. The composition according to claim 1 wherein the other excipients comprise from about 0.1% to about 25% edible acid by weight of the composition.

4. The composition according to claim 3 wherein the edible acid is selected from the group consisting of citric acid, ascorbic acid, malic acid, succinic acid, tartaric acid, phosphoric acid, monopotassium phosphate, and mixtures thereof.

5. A psyllium husk/anion exchange resin-containing drink mix composition comprising:
   (a) from about 20 % to about 90% psyllium husk;
   (b) from about 20 % to about 90% of an anion exchange resin selected from the group consisting of cholestyramine, and mixtures thereof;
   (c) from about 0.1% to about 20 % edible, water soluble salt selected from the group consisting of magnesium sulfate, calcium chloride, calcium sulfate, calcium citrate malate, potassium chloride, sodium chloride, potassium sulfate, sodium sulfate, zinc chloride, zinc sulfate, potassium sorbate, and mixtures thereof, at a level whereby the gellation rate of the psyllium husk/anion exchange resin-containing drink mix composition in an aqueous solution is reduced; and
   (d) from about 1% to about 60% other excipients; and wherein further said composition is in a form mixable with a liquid to form suspension of the psyllium husk and the artion exchange resin.

6. The composition according to claim 5 wherein the other excipients comprise from about 0.1% to about 10% edible acid by weight of the composition.

7. The composition according to claim 6 wherein the other excipients comprise less than about 2% edible acid by weight of the composition.

8. The composition according to claim 1 wherein the other excipients comprise from about 0.1% to about 10% edible acid selected from citric acid, phosphoric acid, and mixtures thereof.

9. The composition according to claim 8 wherein the other excipients comprise less than about 1% edible acid by weight of the composition.

10. A psyllium husk/anion exchange resin-containing drink mix composition comprising:
    (a) from about 10% to about 90% , small particle size psyllium husk having particle sizes distributed such that more than about 80% is smaller than about 45 mesh;
    (b) from about 10% to about 90% of an anion exchange resin which is safe and therapeutically effective for treating hypercholesterolemia;
    (c) from about 0.1% to about 50% edible, water soluble salt selected from the group consisting of magnesium sulfate, calcium chloride, calcium sulfate, calcium citrate malate, potassium chloride, sodium chloride, potassium sulfate, sodium sulfate, zinc chloride, zinc sulfate, potassium sorbate, and mixtures thereof, at a level whereby the gellation rate of the psyllium husk/anion exchange resin-containing drink mix composition in an aqueous solution is reduced; and
    (d) from about 0% to about 90% other excipients; and wherein further said composition is in a form mixable with liquid to form a suspension of the psyllium husk and the anion exchange resin.

11. The composition according to claim 10 wherein the small particle size psyllium husk is distributed such that about 80% smaller than about 60 mesh.

12. The composition according to claim 10 wherein the edible, water soluble salt is selected from the group consisting of magnesium sulfate, calcium sulfate, calcium chloride, zinc sulfate, zinc chloride, and mixtures thereof.

13. The composition according to claim 12 wherein the anion exchange resin is selected from the group consisting of cholestyramine, cholestipol and mixtures thereof.

14. The composition according to claim 13 wherein the other excipients comprise less than about 2% edible acid by weight of the composition.

15. A method for reducing serum cholesterol levels in humans or lower animals, said method comprising orally administering to a human or lower animal in need of such treatment a safe and effective amount of a liquid suspension of the psyllium husk and anion exchange resin-containing composition according to claim 1.

16. A method for reducing serum cholesterol levels in humans or lower animals, said method comprising orally administering to a human or lower animal in need of such treatment a safe and effective amount of a liquid suspension of the psyllium husk and anion exchange resin-containing composition according to claim 5.

17. A method for reducing serum cholesterol levels in humans or lower animals, said method comprising orally administering to a human or lower animal in need of such treatment a safe and effective amount of a liquid suspension of the psyllium husk and anion exchange resin-containing composition according to claim 10.

18. A method for reducing serum cholesterol levels in humans or lower animals, said method comprising orally administering to a human or lower animal in need of such treatment a safe and effective amount of a liquid suspension of the psyllium husk and anion exchange resin-containing composition according to claim 13.

* * * * *